(12) United States Patent
Nipe et al.

(10) Patent No.: US 10,902,577 B2
(45) Date of Patent: *Jan. 26, 2021

(54) SYSTEM AND METHOD FOR HYPERSPECTRAL IMAGE PROCESSING TO IDENTIFY OBJECT

(71) Applicant: Apeel Technology, Inc., Goleta, CA (US)

(72) Inventors: Lars Gustav Magnus Nipe, Uppsala (SE); Abilasha Ramanan, London (GB)

(73) Assignee: Apeel Technology, Inc., Goleta, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/977,085

(22) Filed: May 11, 2018

(65) Prior Publication Data

US 2018/0365820 A1    Dec. 20, 2018

Related U.S. Application Data

(60) Provisional application No. 62/521,950, filed on Jun. 19, 2017.

(51) Int. Cl.
   *G06K 9/00*    (2006.01)
   *G06T 7/00*    (2017.01)
   (Continued)

(52) U.S. Cl.
   CPC .......... *G06T 7/0004* (2013.01); *G01N 33/02* (2013.01); *G06K 9/00664* (2013.01); *G06K 9/42* (2013.01);
   (Continued)

(58) Field of Classification Search
   CPC .. G01N 33/02; G06K 2009/4657; G06K 9/42; G06K 9/46; G06K 9/6202;
   (Continued)

(56) References Cited

U.S. PATENT DOCUMENTS

| 4,645,459 A | 2/1987 | Graf et al. |
| 8,194,072 B2 | 6/2012 | Jones et al. |

(Continued)

FOREIGN PATENT DOCUMENTS

| CN | 202614694 | 12/2012 |
| CN | 103257118 | 8/2013 |

(Continued)

OTHER PUBLICATIONS

Peng et al., "Learning Deep Object Detectors from 3D Models", Oct. 12, 2015, pp. 1-9.*

(Continued)

*Primary Examiner* — Charles T Shedrick
(74) *Attorney, Agent, or Firm* — Fish & Richardson P.C.

(57) ABSTRACT

A system includes a memory and at least one processor to acquire a hyperspectral image of an object by an imaging device, the hyperspectral image of the object comprising a three-dimensional set of images of the object, each image in the set of images representing the object in a wavelength range of the electromagnetic spectrum, normalize the hyperspectral image of the object, select a region of interest in the hyperspectral image, the region of interest comprising at least one image in the set of images, extract spectral features from the region of interest in the hyperspectral image, and compare the spectral features from the region of interest with a plurality of images in a training set to determine particular characteristics of the object.

20 Claims, 6 Drawing Sheets

(51) Int. Cl.
  *G01N 33/02* (2006.01)
  *G06T 7/11* (2017.01)
  *G06K 9/62* (2006.01)
  *G06K 9/42* (2006.01)
  *G06K 9/46* (2006.01)

(52) U.S. Cl.
  CPC ............ *G06K 9/46* (2013.01); *G06K 9/6202* (2013.01); *G06K 9/628* (2013.01); *G06K 9/6274* (2013.01); *G06T 7/11* (2017.01); *G06K 2009/4657* (2013.01); *G06K 2209/17* (2013.01); *G06T 2207/10036* (2013.01); *G06T 2207/20081* (2013.01); *G06T 2207/30128* (2013.01)

(58) Field of Classification Search
  CPC ........... G06K 2209/17; G06K 9/00664; G06K 9/6274; G06K 9/628; G06T 2207/10036; G06T 2207/30128; G06T 7/0004; G06T 7/11; G06T 2207/20081
  See application file for complete search history.

(56) References Cited

U.S. PATENT DOCUMENTS

| | | | |
|---|---|---|---|
| 9,367,909 | B2 | 6/2016 | Tin |
| 9,646,223 | B2 | 5/2017 | Sato |
| 2002/0123977 | A1 | 9/2002 | Raz |
| 2003/0130767 | A1* | 7/2003 | Carroll ................ G05D 1/0094 701/3 |
| 2004/0146615 | A1* | 7/2004 | McDonald ............ G01N 21/85 426/231 |
| 2004/0197012 | A1* | 10/2004 | Bourg, Jr. ............. G06T 7/0004 382/110 |
| 2005/0287252 | A1 | 12/2005 | Schrock et al. |
| 2008/0199080 | A1 | 8/2008 | Subbiah et al. |
| 2012/0253749 | A1 | 10/2012 | Bernard et al. |
| 2013/0141530 | A1 | 6/2013 | Zavesky |
| 2014/0137877 | A1* | 5/2014 | Deevi ................ B07C 5/366 131/290 |
| 2014/0267684 | A1 | 9/2014 | Nelson et al. |
| 2016/0162760 | A1 | 6/2016 | Skaff et al. |
| 2016/0239953 | A1 | 8/2016 | Ngadi et al. |
| 2016/0356704 | A1 | 12/2016 | Kim et al. |
| 2017/0178220 | A1* | 6/2017 | Chong ............... G06K 9/00268 |
| 2018/0126901 | A1* | 5/2018 | Levkova ............... B60Q 9/00 |
| 2018/0172516 | A1* | 6/2018 | Jussila ................ G01J 3/2823 |
| 2018/0365820 | A1* | 12/2018 | Nipe .................. G06K 9/00664 |
| 2018/0365822 | A1* | 12/2018 | Nipe ...................... G06K 9/42 |
| 2019/0096049 | A1* | 3/2019 | Kim ..................... G06N 3/084 |
| 2019/0311230 | A1* | 10/2019 | Mahapatra ........... G06N 3/0454 |
| 2019/0340749 | A1* | 11/2019 | Schwartzer ......... G01N 21/255 |

FOREIGN PATENT DOCUMENTS

| | | |
|---|---|---|
| CN | 103439285 | 12/2013 |
| DE | 102008046988 | 4/2010 |
| WO | 2006116386 | 11/2006 |
| WO | 200768056 A1 | 6/2007 |
| WO | 2012074372 | 6/2012 |
| WO | 2014078858 | 5/2014 |

OTHER PUBLICATIONS

J. Talukdar, A. Biswas and S. Gupta, "Data Augmentation on Synthetic Images for Transfer Learning using Deep CNNs," 2018 5th International Conference on Signal Processing and Integrated Networks (SPIN), Noida, 2018, pp. 215-219, doi: 10.1109/SPIN.2018.8474209.*

International Search Report and Written Opinion regarding PCT/US2018/038246 dated Sep. 5, 2018, 8 pages.

Valenzuela et al., Assessment of External and Internal Quality of Blueberries Using Images, Aug. 7, 2013, Santiago de Chile, Chile, 93 pages.

* cited by examiner

SYSTEM AND METHOD FOR HYPERSPECTRAL IMAGE PROCESSING TO IDENTIFY OBJECT

CROSS-REFERENCE TO RELATED APPLICATIONS

This application is related to and claims priority under 35 U.S.C. § 119(e) to U.S. Patent Application No. 62/521,950, filed Jun. 19, 2017, entitled "SYSTEM AND METHOD FOR CLASSIFYING QUALITY PARAMETERS OF AVOCADOS DURING SUPPLY CHAIN PROCESSES," the entire contents of which are incorporated herein by reference.

BACKGROUND

Food quality and safety, in addition to food traceability and authenticity are issues of the highest economic and environmental importance for consumers, governments, and the food industry. Visual inspections, sample tests, and traditional microbiological and DNA-based tests are no longer adequate monitoring tools to ensure security in increasingly complex food supply chains. The development and application of rapid, non-destructive and accurate quality assurance systems based on controlling, monitoring, and recording the critical parameters throughout the food supply chain are crucial for both food quality and safety applications.

For food producers and retailers, the quality control and quality assurance process today involves time-consuming visual inspections, sample tests, and expensive and lengthy lab-based microbiological sampling, resulting in contaminants such as plastics, metals, fibers, and other contaminants being found in finished food products leading to recalls, loss of sales, and brand and reputational damage. The global food industry is in need of a rapid, non-invasive, and accurate system for detecting contaminants during processing to increase the security and transparency of supply chains.

Conventional food quality and safety control is overwhelmingly analog and varies significantly between food companies. Food companies use a myriad of different outdated methodologies. Quality control and quality assurance is highly dependent on visual inspections, destructive tests and sample-based testings, resulting in high levels of waste and increasing levels of fraud and contamination.

It is with these issues in mind, among others, that various aspects of the disclosure were conceived.

SUMMARY

According to one aspect, a system for hyperspectral image processing is provided for performing hyperspectral image processing on a hyperspectral image of an object comprising a set of images of the object to compare a region of interest in the hyperspectral image with a plurality of images in a training set. As a result, the system may determine characteristics of the object by comparing the region of interest in the hyperspectral image with the plurality of images in the training set. The system may include memory and at least one processor to acquire a hyperspectral image of an object by an imaging device, the hyperspectral image of the object comprising a three-dimensional set of images of the object, each image in the set of images representing the object in a wavelength range of the electromagnetic spectrum, normalize the hyperspectral image of the object, select a region of interest in the hyperspectral image, the region of interest comprising a subset of at least one image in the set of images, extract spectral features from the region of interest in the hyperspectral image, compare the spectral features from the region of interest with a plurality of images in a training set to determine particular characteristics of the object, and identify the object based on the spectral features.

According to another aspect, a method includes acquiring, by a processor, a hyperspectral image of an object by an imaging device, the hyperspectral image of the object comprising a three-dimensional set of images of the object, each image in the set of images representing the object in a wavelength range of the electromagnetic spectrum, normalizing, by the processor, the hyperspectral image of the object, selecting, by the processor, a region of interest in the hyperspectral image, the region of interest comprising a subset of at least one image in the set of images, extracting, by the processor, spectral features from the region of interest in the hyperspectral image, comparing, by the processor, the spectral features from the region of interest with a plurality of images in a training set to determine particular characteristics of the object, and identifying the object based on the spectral features.

According to an additional aspect, a non-transitory computer-readable storage medium includes instructions stored thereon that, when executed by a computing device cause the computing device to perform operations, the operations including acquiring a hyperspectral image of an object by an imaging device, the hyperspectral image of the object comprising a three-dimensional set of images of the object, each image in the set of images representing the object in a wavelength range of the electromagnetic spectrum, normalizing the hyperspectral image of the object, selecting a region of interest in the hyperspectral image, the region of interest comprising a subset of at least one image in the set of images, extracting spectral features from the region of interest in the hyperspectral image, comparing the spectral features from the region of interest with a plurality of images in a training set to determine particular characteristics of the object, and identify the object based on the spectral features.

These and other aspects, features, and benefits of the present disclosure will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE DRAWINGS

The accompanying drawings illustrate embodiments and/or aspects of the disclosure and, together with the written description, serve to explain the principles of the disclosure. Wherever possible, the same reference numbers are used throughout the drawings to refer to the same or like elements of an embodiment, and wherein.

DETAILED DESCRIPTION

Figure 1:
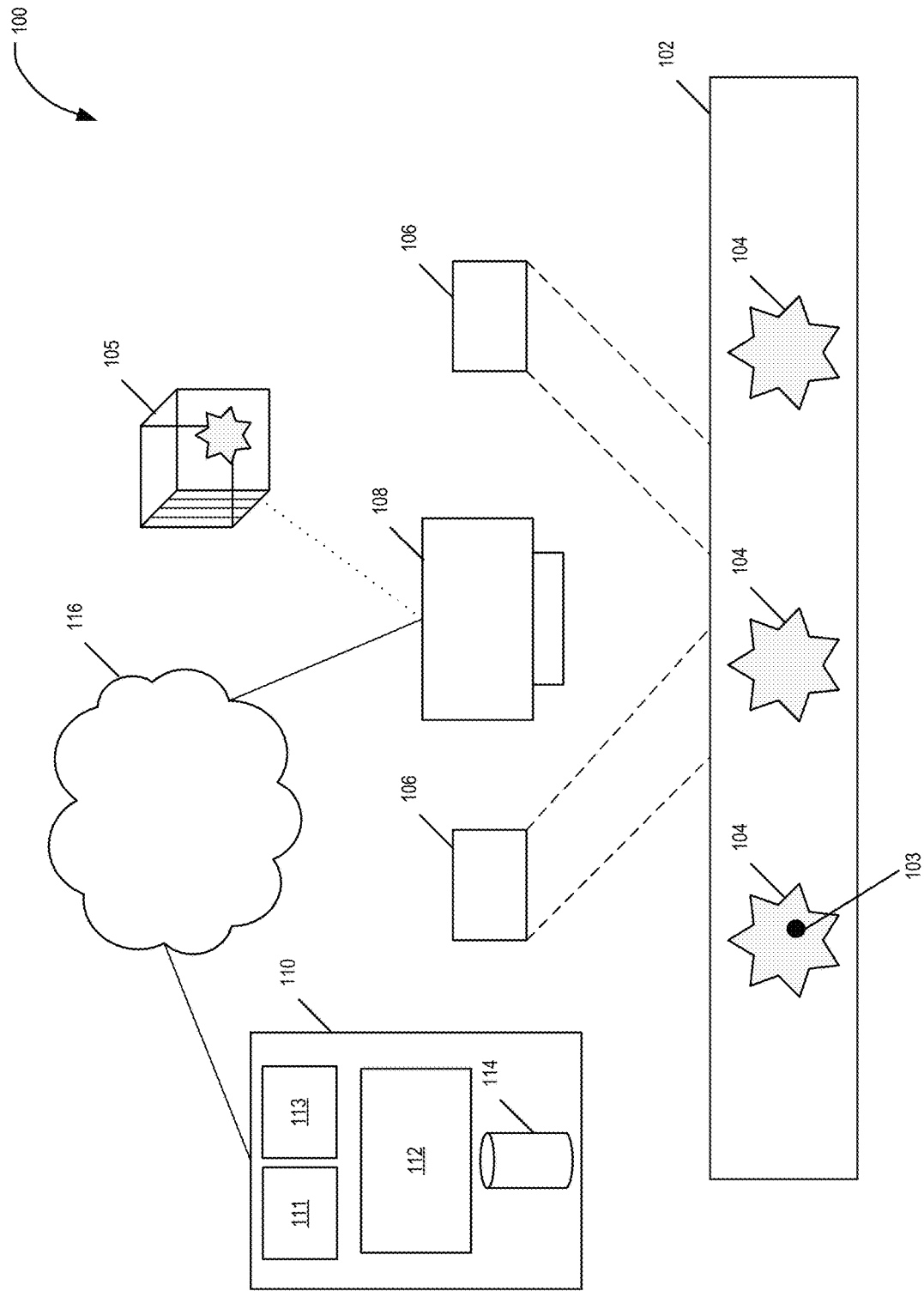
FIG. 1 is a block diagram of a system for hyperspectral image processing according to an example embodiment.

Aspects of a system and method for hyperspectral image processing provide a computing device executing an image processing application for hyperspectral image processing on a hyperspectral image of an object comprising a set of images of the object to compare a region of interest in the hyperspectral image with a plurality of images in a training set. This may be used to classify quality of the object with respect to one or more factors or parameters and may be used to classify quality of a perishable item such as a type of food during food supply chain processes. In one example, the object may be a food object such as an avocado. As a result, the application may determine characteristics of the object by comparing the region of interest in the hyperspectral image with the plurality of images in the training set. The computing device may be in communication with an imaging device that captures the hyperspectral image of the object. The object may be one object of a plurality of objects that are located on a conveyor belt that is illuminated by at least one illumination device and move past the imaging device.

The object may be a food object or agricultural product such as one of the avocado, a banana, an orange, a peach, an onion, a pear, a kiwi fruit, a mango, berries, a tomato, an apple, sugar, pork, lamb, beef, or fish, among other objects. In addition, the imaging device may determine that there is a contaminant or a foreign object in the image.

The system includes memory and at least one processor to acquire the hyperspectral image of the object by the imaging device, the hyperspectral image of the object comprising a three-dimensional set of images of the object, each image in the set of images representing the object in a wavelength range of the electromagnetic spectrum, normalize the hyperspectral image of the object, select a region of interest in the hyperspectral image, the region of interest comprising a subset of at least one image in the set of images, extract spectral features from the region of interest in the hyperspectral image, and compare the spectral features from the region of interest with a plurality of images in a training set to determine particular characteristics of the object.

In one aspect, the system is provided for using hyperspectral imaging to determine Dry Matter content of an object such as an avocado or another perishable item. In another aspect, the system is provided for using hyperspectral imaging to determine firmness of an object such as an avocado or another perishable item. In another aspect, the system is provided for using hyperspectral imaging to determine ripeness of an object such as an avocado or another perishable item.

In another aspect, the system is provided for using hyperspectral imaging to determine the presence of a contaminant such as an object that should not be located on the conveyor belt. This may be a foreign object. The contaminant may be one of plastic, paper, a metal hook, a cigarette butt, cardboard, textile, or another type of contaminant. As an example, the plastic contaminant may be plastic parts such as a cable tie.

The system may include an imaging module for acquiring a hyperspectral image of at least a portion of the object, a pre-processing module for analyzing the hyperspectral image to generate data that can be processed, and an output module for providing output regarding the analysis of the hyperspectral image. In one example, the hyperspectral image may be a set of images that together form a hyperspectral data cube to be processed by the system. The set of images may include two hundred and twenty four images of the object that each represents a range of wavelengths in the hyperspectral image. Alternatively, the set of images may include a different number of images that each represents a range of wavelengths in the hyperspectral image.

The system may additionally include a synthetic data generation module that may be used to create a training set for determining characteristics of the object and may generate a database of data or library of data. The hyperspectral image captured by the imaging module may be compared with the database of data to analyze the hyperspectral image.

As noted herein, conventional food quality and safety control is overwhelmingly analog and varies significantly between food companies. Food companies use a myriad of different outdated methodologies. Quality control and quality assurance is highly dependent on visual inspections, and destructive tests and samples, resulting in high levels of waste and increasing levels of fraud and contamination.

Further, for food producers and retailers, the quality control and quality assurance process today involves time-consuming visual inspections, sample tests, and expensive and lengthy lab-based microbiological sampling, resulting in contaminants such as plastics, metals, fibers, and other contaminants being found in finished food products leading to recalls, loss of sales, and brand and reputational damage. The global food industry is in need of a rapid-non-invasive and accurate system for detecting contaminants during processing to increase the security and transparency of supply chains.

The problems associated with the destructive and conventional tests of an object such as a perishable food item may be solved by a computing device that performs hyperspectral image analysis of the object to determine characteristics of the object without destroying the object. Thus, the solutions discussed herein provide efficiencies and financial benefits for the food industry. The computing device may execute a hyperspectral image processing application that provides solutions that human visual inspections cannot provide. The computing device is able to quickly and efficiently analyze a plurality of perishable food items by comparing hyperspectral images of the perishable food items to a library or database of images and using machine learning to improve the analysis.

The library or database of images may be based on actual objects and/or may be rendered by the computing device. The rendered images may be based on actual objects that may be augmented with data inserted in the images by the computing device or modified by the computing device. As an example, the data inserted into the images may be color data. Alternatively, the object may be modified in a way such as to modify an orientation and/or a position of the object in the image. Each image in the library or database of images may have associated information such as characteristics of the object.

FIG. 1 shows a block diagram of a system for hyperspectral image processing 100 for identifying an object and for classifying quality parameters of an object according to an example embodiment. The system for hyperspectral image processing 100 may include a moving tray or a conveyor belt device 102 having one or more objects 104 that travel along the moving tray or a conveyor belt of the conveyor belt device 102. The one or more objects may have a foreign object 103 or contaminant on them. In addition, the system for hyperspectral image processing 100 may include an illumination system that may include at least one illumination device 106.

Additionally, the system for hyperspectral image processing 100 may include at least one imaging device 108. In one example, the imaging device 108 may be a chemical machine vision camera such as a hyperspectral camera that may include one or more optical sensors configured to detect electromagnetic energy that is incident on the sensor. Any number of various optical sensors may be used to obtain images in various spectral regions for use in analyzing properties of the one or more objects 104. As an example, the imaging device 104 may be configured to collect images in the 400-1000 nanometer (nm) wavelength region, which corresponds to visible and near-infrared light.

Thus, the imaging device 108 may collect information incident on the sensor as a set of images 105, whereby each image in the set of images represents a wavelength range of the electromagnetic spectrum. Each image of the set of images 105 may represent a spectral band. As shown in FIG. 1, the set of images 105 may be combined together to form a three-dimensional data cube for processing and analysis by the computing device 110. The x and y dimensions of each image in the set of images may represent two spatial dimensions of the object 104 on the conveyor belt device 102 and the wavelength dimension in the cube may represent the spectral dimension that comprises a range of wavelengths in the image.

The object 104 may sit on the moving tray or the conveyor belt device 102 and the moving tray or the conveyor belt device 102 may include a linear slide to move each object 104 past the imaging device 108. The imaging device 108 may be a line scanner camera such that the imaging device 108 may acquire an image by moving the object in a steady, straight, and continuous motion under the sensor at a constant speed. As an example, if the object 104 is a piece of frozen fish, then moving the frozen fish on a conveyor belt underneath the imaging device 108 may allow the imaging device to scan the entire frozen fish.

Alternatively, the imaging device 108 may be a push broom scanner or a snapshot imager. In one example, the moving tray or the conveyor belt device 102 may include a motor such as a stepper motor.

Additionally, the system for hyperspectral image processing 100 may include a computing device 110 for performing hyperspectral image processing on the hyperspectral image 105 captured by the at least one imaging device 108. Additionally, the computing device 110 may be used to synchronize the operation of the imaging device 108 with the operation of the moving tray or the conveyor belt device 102.

The illumination device 106 may be a concentrated light source that may direct electromagnetic energy at the one or more objects 104. The concentrated light source may be configured to direct a particular wavelength of light at an object, after which the at least one imaging device 108 may detect reflected light from the at least one illumination device 106. The at least one illumination device may be a light source such as a halogen light or another light source. In addition, the at least one light source 106 may direct light toward the object 104 to provide uniform illumination of the object. In one example, there may be two light sources 106 that direct light at a forty-five degree angle to the object 104 being imaged. The two light sources 106 may face one another. Other arrangements of the light sources 106 are possible.

The computing device 110 may include an image processing application 112 that processes and analyzes each hyperspectral image 105 captured by the imaging device 108. The computing device 110 may include and/or be in communication with a database 114 that may store data and images associated with the system for hyperspectral image processing 100. In one example, the database 114 may store information such as a training set of data that may comprise a plurality of images of the object 104. The plurality of images may be generated synthetically by the computing device 110 and/or obtained from another source. In addition, the plurality of images may be captured by the imaging device 108 and included as part of the training set of data. Additionally, the database may store characteristics of the object in each of the plurality of images. These characteristics may include a label or name for the object and other information such as measurements of the object. The measurements may be assigned manually by users of the computing device 110 and/or determined automatically by the computing device 110 during analysis of the hyperspectral image 105. As an example, the measurements may be ground truth measurements of the object 104. Additionally, the image processing application 112 may communicate with other computing devices via a communication network 116.

The at least one computing device 110 is configured to receive data from and/or transmit data to other computing devices through the communication network 116. As an example, the imaging device 108 may transmit each hyperspectral image 105 to the computing device 110 for analysis. Although the at least one computing device 110 is shown as a single computing device, it is contemplated that the at least one computing device may include multiple computing devices, for example, in a cloud computing configuration. Additionally, the at least one computing device 110 is configured to receive data and/or transmit data through the communication network 116.

The communication network 116 can be the Internet, an intranet, or another wired or wireless communication network. For example, the communication network 106 may include a Mobile Communications (GSM) network, a code division multiple access (CDMA) network, $3^{rd}$ Generation Partnership Project (GPP), an Internet Protocol (IP) network, a wireless application protocol (WAP) network, a WiFi network, or an IEEE 802.11 standards network, as well as various communications thereof. Other conventional and/or later developed wired and wireless networks may also be used.

The at least one computing device 110 includes at least one processor 111 to process data and memory 113 to store data. The processor 111 processes communications, builds communications, retrieves data from memory 113, and stores data to memory 113. The processor 111 and the memory 113 are hardware. The memory 113 may include volatile and/or non-volatile memory, e.g., a computer-readable storage medium such as a cache, random access memory (RAM), read only memory (ROM), flash memory, or other memory to store data and/or computer-readable executable instructions such as a portion or component of the image processing application 112. In addition, the at least one computing device 110 further includes at least one communications interface to transmit and receive communications, messages, and/or signals.

The at least one computing device 110 may display on a display a graphical user interface (or GUI) to generate a graphical user interface on the display. The graphical user interface may be provided by the image processing application 112. The graphical user interface enables a user of the at least one computing device 110 to interact with the at least one computing device 110 and the image processing application 112.

The GUI may be a component of an application and/or service executable by the at least one computing device 110. For example, the image processing application 112 may be a single unit of deployable executable code or a plurality of units of deployable executable code. According to one aspect, the image processing application 112 may be a web application, a native application, and/or a mobile application (e.g., an app) downloaded from a digital distribution application platform that allows users to browse and download applications developed with software development kits (SDKs) including the App Store and GOOGLE PLAY®, among others. The image processing application 112 or at least a portion thereof may be resident and executed by the at least one computing device 110, which may have the WINDOWS® operating system, a Linux-based operating system, the OS X® operating system, the iOS operating system, or an ANDROID™ operating system, among other operating systems.

Figure 2:
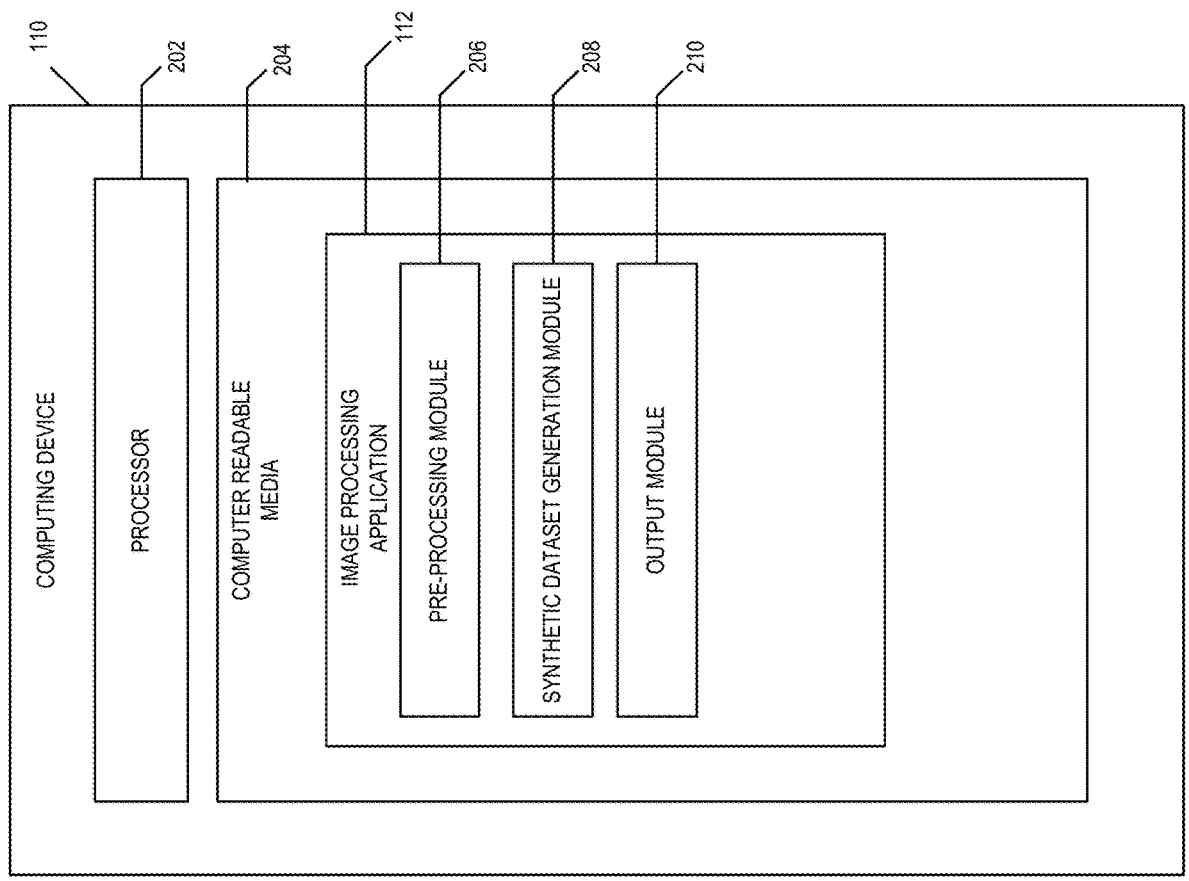
FIG. 2 illustrates a block diagram of a computing device of the system according to an example embodiment.

FIG. 2 illustrates a block diagram of the computing device 110 according to an example embodiment. The computing device 110 may be a computer having a processor 202, such as a laptop, desktop, tablet computer, mobile computing device (e.g., a smartphone), a wearable device, or a dedicated electronic device having a processor and memory. The one or more processors 202 process machine/computer-readable executable instructions and data, and the memory stores machine/computer-readable executable instructions and data including one or more applications, including the image processing application 112. The processor 202 and memory are hardware. The memory includes random access memory (RAM) and non-transitory memory, e.g., a non-transitory computer-readable storage medium such as one or more flash storages or hard drives. The non-transitory memory may include any tangible computer-readable medium including, for example, magnetic and/or optical disks, flash drives, and the like. Additionally, the memory may also include a dedicated file server having one or more dedicated processors, random access memory (RAM), a Redundant Array of Inexpensive/Independent Disks (RAID) hard drive configuration, and an Ethernet interface or other communication interface, among other components.

The computing device 110 includes computer readable media (CRM) 204 in memory on which the image processing application 112 or other user interface or application is stored. The computer readable media may include volatile media, nonvolatile media, removable media, non-removable media, and/or another available medium that can be accessed by the processor 202. By way of example and not limitation, the computer readable media comprises computer storage media and communication media. Computer storage media includes non-transitory storage memory, volatile media, nonvolatile media, removable media, and/or non-removable media implemented in a method or technology for storage of information, such as computer/machine-readable/executable instructions, data structures, program modules, or other data. Communication media may embody computer/machine-readable/executable instructions, data structures, program modules, or other data and include an information delivery media or system, both of which are hardware.

As shown in FIG. 2, the image processing application 112 may include a pre-processing module 206 that may receive an image from the imaging device 108 and perform pre-processing on the image. First, the pre-processing module 206 may perform pre-processing on the image using one or more sub-modules. The sub-modules may include a normalization module that may perform normalization on the image, object recognition using an object recognition module, feature extraction using a feature extraction module, and reduction of data using a reduction of data module.

The normalization of the image may be performed to compare images that may have a different level of illumination. The normalization of the captured spectral data may include black level subtraction combined with white level normalization. When using a linear push broom sensor array, the normalization may be performed per-sampling elements to account for spatially variant, static noise. Other sensor types may use normalization specific to their design. Normalization may also include removing the illuminant spectrum based on an estimate of the illuminant from a separate sensing apparatus. The feature extraction module may extract bags of features including but not limited to spatial features including maximally stable extremal regions, Haralick textural features, FAST (Features from Accelerated Segment Test) corner features, and spectral features including dimensionality reduced spectra, selected spectral ranges, and interpolated spectral values. The feature extraction module may combine spatial and spectral features to determine specific quality parameter classification. The object recognition module may utilize machine learning, including but not limited to neural networks to detect and classify objects in the image.

The reduction of data module may reduce dimensionality of data in the image. This may be performed by performing principal component (PC) analysis or another type of analysis. In other words, the pre-processing module 206 may reduce redundancies in the image and may eliminate some of the images in the set of images captured by the imaging device 108 that is unnecessary for performing the image processing. Certain wavelength ranges may be more useful for the image processing and analysis than others. As an example, if the set of images includes two hundred and twenty four different images that each represent a different wavelength range of the object, then the pre-preprocessing module 206 may select ten of the two hundred and twenty four different images as the images that best represent the object in the set of images. In other words, the pre-processing module 206 may select a subset of the set of images that best represent the object and/or spectral features of the object in the set of images.

Additionally, the image processing application 112 may include a synthetic dataset generation module 208 that may generate a plurality of training data for deriving a mathematical model that may represent content in the data. Neural network models have a tendency to overfit data. In other words, neural network models may be sensitive to training data and behavior of the model may not generalize to new/unseen data. One way to avoid overfitting is to collect a large amount of data. A typical neural network may have up to one million parameters, and tuning these parameters may require millions of training instances of uncorrelated data, which may not always be possible and in some cases may be cost prohibitive to software development. These issues may be addressed through the use of the synthetic dataset generation module 208 by classifying different materials associated with objects and foreign objects in thousands of shapes and formations. One such way to avoid overfitting other than collecting a large amount of data may be to utilize data augmentation. Augmentation refers to the process of generating new training data from a smaller data set such that the new data set represents the real world data that one may see used in practice.

The synthetic dataset generation module 208 may be provided with ground truth measurements on each object so that the output module 210 may correlate a specific image captured by the imaging device 108 with a specific ground truth measurement value. A ground truth measurement may be a chemical or physical test of a characteristic such as pH or tenderness of an object. Thus, the computing device 110 is able to use machine learning on images from the synthetic dataset generation module 208 and images obtained by the imaging device 108 to continue to improve and compare images.

Data mirroring and cropping may be used as specific techniques for data augmentation in computer vision and image processing. Image data may be represented in a variety of different orientations. In other words, copies of a same image may be generated from different perspectives or visual angles.

As an example, training data associated with the synthetic dataset generation module 208 may be built by obtaining and/or simulating images of an object or agricultural product such as an avocado, a banana, an orange, a peach, an onion, a pear, a kiwi fruit, a mango, berries, a tomato, an apple, sugar, pork, lamb, beef, or fish, among other objects. The training data may be stored in the database 114 and/or memory of the computing device 110, among other locations.

Different colors of a banana may indicate different firmness levels. A banana may be represented as a color coded landscape, e.g., where green fields may indicate a firm banana. Different colors of an avocado may indicate different firmness levels.

In addition, the image processing application 112 may be able to determine bruises or defects associated with an orange. The image processing application 112 may be able to determine a cold injury on a peach or sour skin disease in an onion.

Additionally, the image processing application 112 may be able to determine bruises or defects associated with a kiwi fruit or a pear. Further, the image processing application 112 may be able to determine issues associated with other types of citrus fruits such as a citrus canker.

In addition, the image processing application 112 may be able to determine freshness of a fish by providing analysis of a fish eye. The image processing application 112 may be able to determine tenderness of pork, lamb, beef, or another type of meat product.

As an example, the synthetic dataset generation module 208 may generate a synthetic dataset for beef tenderness. The intramuscular fat of beef may have a strong implication on tenderness of a beef steak. The intramuscular fat may be viewed as rivers or a delta in a landscape with different altitudes. The synthetic dataset may include rendered landscapes (images) with rivers and deltas having steaks with different tenderness classes. A rendered image may appear as a hyperspectral image that has been created by the computing device 110 or another computing device. Using the synthetic beef images, the computing device 110 may extract spectral features from images of beef steak. The synthetic spectral features may be fed into a classifier of the synthetic dataset generation module 208 to further improve and develop the training data, thereby resulting in better prediction accuracy.

As an example, acquiring three hundred cuts of beef and performing ground truth measurements on the cuts of beef may take approximately one month for a beef producer. This may be a full time job for one person. If each cut of beef costs $10.00 and the cost to pay the producer may be $4,700, then this would cost $7,700. This is only the cost for one type of beef cut and the system would have to be applicable to a plurality of different beef cuts from multiple different muscles. Thus, in order to provide a model suitable for the system, the system would have to utilize different images from different beef producers.

To create a best model for beef tenderness, in theory, it would be desirable to have 10,000 beef images. Thus, this would cost $78,000 only to collect and obtain data. However, the synthetic dataset generation module 208 may generate training data from a smaller set of data to solve financial and efficiency issues. This may save on database storage and may provide computing efficiency savings. It may be estimated that the synthetic dataset generation module 208 may significantly reduce costs to nearly zero once samples for initial training have been tested.

As another example, the synthetic dataset generation module 208 may obtain pixels from an image set that may be correlated with different quality parameters of an object 104 such as a fruit. Certain brown and yellow pixels may be used to determine particular ripeness levels of the banana. The synthetic dataset generation module 208 may be able to manipulate and replicate the brown and yellow pixels in a plurality of different positions to simulate and create images indicating different stages of ripeness for bananas. As an example, the synthetic dataset generation module 208 may use a hyperspectral image of a very ripe banana having a plurality of brown pixels. In addition, the synthetic dataset generation module 208 may have another hyperspectral image of an unripe banana having yellow and green pixels. The synthetic dataset generation module 208 may generate a new image based on these images of the very ripe banana and the unripe banana that is somewhat between the two images.

The synthetic dataset generation module 208 may receive an image captured by the imaging device 108 or from another source and may add information and data to the image by augmenting the image. As an example, the synthetic dataset generation module 208 may manipulate the image by adding color to pixels to an image. An avocado may have pixels of a certain color. By adding additional very green color to pixels to the image, the synthetic dataset generation module 208 may change a ripeness level of the avocado. Each image captured by the imaging device may have a plurality of channels and thus each pixel may have a plurality of associated data points.

As another example, the synthetic dataset generation module 208 may digitally add and/or modify an object in the image by inserting spectral information into the image. The synthetic dataset generation module 208 may automatically manipulate the object to render the object in a different position and/or orientation.

Even further, the synthetic dataset generation module 208 may insert a foreign object into the image by inserting the foreign object on the object 104. The foreign material or object may be injected into the image at a known location. Then, sampling the spectra from the regions/pixels affected by the object may provide a frequency table that indicates the foreign material. The synthetic dataset generation module 208 may increase a size of data matrices by seeding known data ("infected") points. This may allow the synthetic dataset generation module 208 to generate a lot of data points with a small differentiation from real values collected.

The matrices may then be used to create areas of simulated hidden foreign bodies and the neural network may be trained.

As an example, different colors of plastic or paper objects may be rendered on or into the object to make it appear that the object has one or more foreign objects or materials. The synthetic dataset generation module 208 may manipulate the one or more foreign objects and may manipulate the foreign object in a plurality of different positions and/or orientations. Thus, the synthetic dataset generation module 208 may automatically generate and modify images by augmenting images.

In one example, the synthetic dataset generation module 208 may generate a three dimensional model of one or more objects to be detected. Real world objects may be used as reference. Animations of the objects may be rendered with variations in size, orientation, visibility, occlusion, deformation, and background (noise). The synthetic dataset generation module 208 may utilize pre-trained networks to obtain higher precision and reduce an amount of compute resources used. The shape of the distribution of sampled pixels may be "roughly" determined by generating new pixels by "filling in" more pixel data that does not disturb a general shape of an associated frequency table. This may allow the synthetic dataset generation module 208 to properly parameterize learning/network models based on real data and include augmented data. The robustness of the networks may be manually tuned by a user by modifying a range of normalized stochastic variables that may be used in seeding generated matrices in conjunction with tuning parameters of the networks.

Further, the image processing application 112 may include an output module 210. The output module 210 may perform machine learning classification of an object and predict and assign quality parameters to objects. The output module 210 may receive the hyperspectral image 105 from the pre-processing module 206 that has been pre-processed and receive the synthetic dataset from the synthetic dataset generation module 208. The output module 210 may compare a region of interest in the hyperspectral image 105 with the training set of data that may comprise the plurality of images of the object 104 that may include the synthetic dataset. The output module 210 may include one or more sub-modules that may include a machine learning classification module that may utilize generative adversarial neural networks and/or deep learning neural networks to classify bags of features. The machine learning classification module may also utilize a partial least squares regression to classify bags of features. In addition, other classification models may be used to classify bags of features.

The output module 210 may add an object label and may determine that pixels in the hyperspectral image have spectral information indicating quality information. The output module 210 may perform object recognition on a selected region of interest in the image. A region of interest may be a specific area of an image that may include information of value for determining a quality of an object. As an example, the region of interest may be selected by obtaining a hyperspectral image 105 of an object from the imaging device 108. The object may be an avocado or another object. The region of interest may be determined automatically using gray scaling or edge detection. As an example, with gray scaling, the entire image may be converted into pixels which have a gray color value between zero and one. The output module 210 may set a threshold value to enable the computing device 110 to differentiate between the object and the conveyor belt.

Once the region of interest is identified, the output module 210 may extract all spectral information from pixels in the region of interest. Spectral information may be extracted from each pixel in the region of interest and the spectral information for determining each pixel in the region of interest and may be stored as a table associated with the image. Once all of the pixels have been classified, the output module 210 may compare each pixel with neighbors to determine if the pixels have neighboring pixels with a same classification. If a pixel has more than one neighbor, the pixel may be classified as a foreign object. Alternatively, if a pixel has at least three neighbors or at least N neighbors, the pixel may be classified as a foreign object. In addition, the output module 210 may determine a spatial value for the pixel by counting the number of pixels that are neighbors. This may be used to determine a dimensionality. In other words, if a pixel is known to represent one inch by one inch on the conveyor belt, then by determining a number of pixels are classified and are neighbors, the output module 210 may measure a dimensionality of the object.

The pixels may be used to train the output module 210 and/or to recognize quality attributes of the object. All spectral data provided to the machine learning classification module may be reduced to match a minimum viable set of features thereby allowing imaging systems that may not share exact specifications. As an example, the minimum viable set of features may be features that may be determined by different hyperspectral imaging systems. One hyperspectral system may extract spectral values between 400 nanometers and 600 nanometers. A second hyperspectral system may extract spectral values between 400 nanometers and 1000 nanometers. The minimum viable set of features between the first hyperspectral system and the second hyperspectral system may be 400 nanometers to 600 nanometers. That may allow the computing device 110 to detect patterns between spectral values and a ripeness quality of an object such as an avocado. The output module 210 may further perform extraction of spectral data from the object.

In addition, before classifying the image as representing a specific object having certain qualities, the output module 210 may reduce data in the image by compressing data associated with the image. This may include generating a mean value of the spectral values in the region of interest. The mean may be a mean for the entire region of interest or a spectral mean for each pixel.

The machine learning classification may have four layers including one input layer, two hidden layers, and one output layer. In one aspect, the machine learning classification may utilize a neural network that may have three autoencoder layers, whereby the first layer may act as the input layer and the remaining layers may be hidden layers. The autoencoder layers may together form a stacked autoencoder (SAE). The autoencoder layers may further include a logistic regression layer and an output layer that may return class probabilities.

A user of the system 100 may initially train the machine learning classification module by assigning a label (e.g., avocado) and quality parameter information (e.g., firmness, dry matter content, amount of sugar) to one or more sets of images. The quality parameter information may be based on ground truth measurements of the object captured in the one or more sets of images. The machine learning classification module may use this initial training data to develop a mathematical model that allows the machine learning classification module to assign a particular label and quality parameter information to an input image by comparing the input image to each image in the training data. The machine learning classification module may then add the input image to the training data and learn from this input image to continue to perform more precise assignment of the label and quality parameter information.

In one example, the machine learning classification module may utilize libraries associated with a machine learning framework such as TENSORFLOW™ or another machine learning framework. In another example, the machine learning classification module may utilize one or more support vector machines (SVMs) to classify the object 104 in the image.

Figure 3:
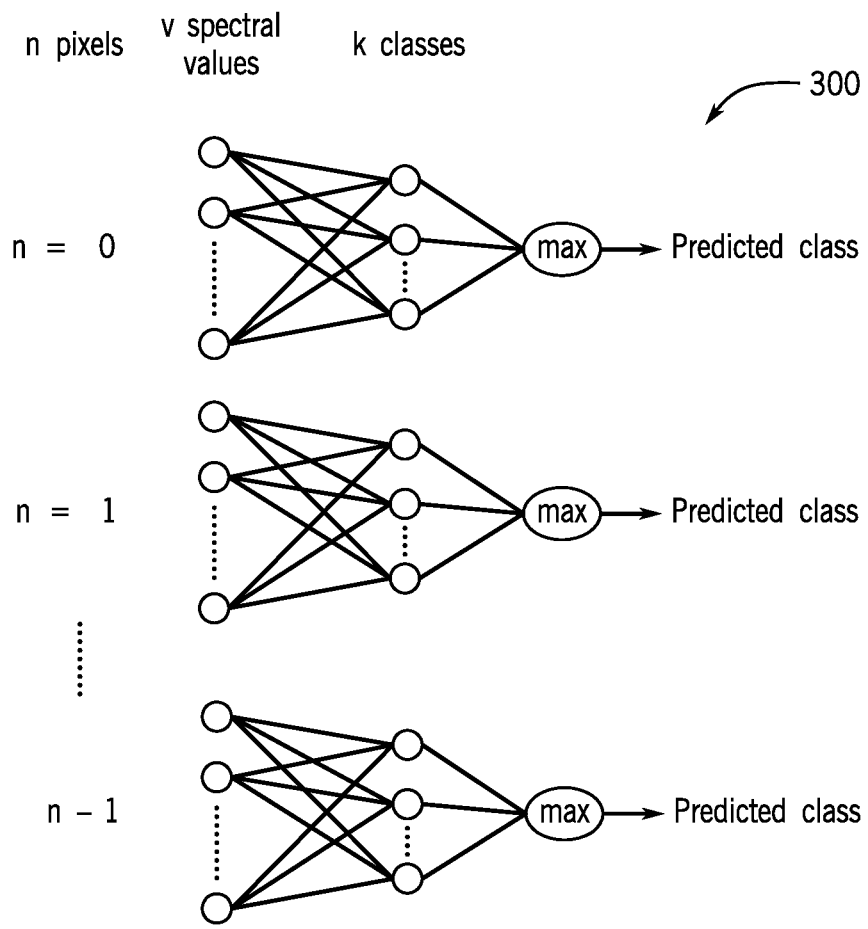
FIG. 3 illustrates a flowchart for performing machine learning classification on an image according to an example embodiment.

FIG. 3 illustrates an example process 300 of performing machine learning classification on the hyperspectral image 105 according to an example embodiment. As shown in FIG. 3, the output module 210 may determine that there are n pixels in the image. For each pixel of the n pixels in the image, the output module 210 may determine that there are v spectral values. Each of the v spectral values for the pixel may be fed into a classifier provided by the output module 210. The classifier may determine that the v spectral values are associated with k classes. For each class of the k classes, the output module 210 may determine a dot product for each of the pixel's spectral values and the class. A class having a highest value is determined to be a predicted class for the image 105.

The output module 210 may identify and determine the label for each object and assign quality parameters to the object based on analysis of the image set. The output module 210 may determine characteristics of the object 104 by comparing the region of interest in the hyperspectral image 105 with the plurality of images in the training set. The analysis of the image may be based on the comparison of the image set with the data provided by the machine learning classification module. As an example, the output module 210 may determine approximate measurements for the object. If the object is a fruit such as an avocado then the measurements may include a firmness, a dry matter content, and a sugar content. Other measurements are possible based on the object 104 to be analyzed.

Firmness may be measured using the Anderson Firmometer measure. A typical firmness value of an avocado immediately post-harvest may be ten to fifteen, wherein the scale ranges from zero to one-hundred and ten. Firmness may indicate a ripeness level.

Dry matter content may be an indicator for ripeness of an object such as an avocado. Dry matter may be measured as a percentage of the avocado, wherein a typical value may be twenty-one percent.

The amount of sugar in an object such as avocado may be estimated using a high-performance liquid chromatography-test (HPLC), which is an analytical chemical tool. The amount of sugar may indicate a ripeness of the fruit. A higher concentration of sugar in the fruit may indicate that it is riper. A sugar content may be measured as an amount of sugar per one hundred grams. A typical value of sugar content in an avocado may be 0.9 grams of sugar per one hundred grams of avocado.

Figure 4:
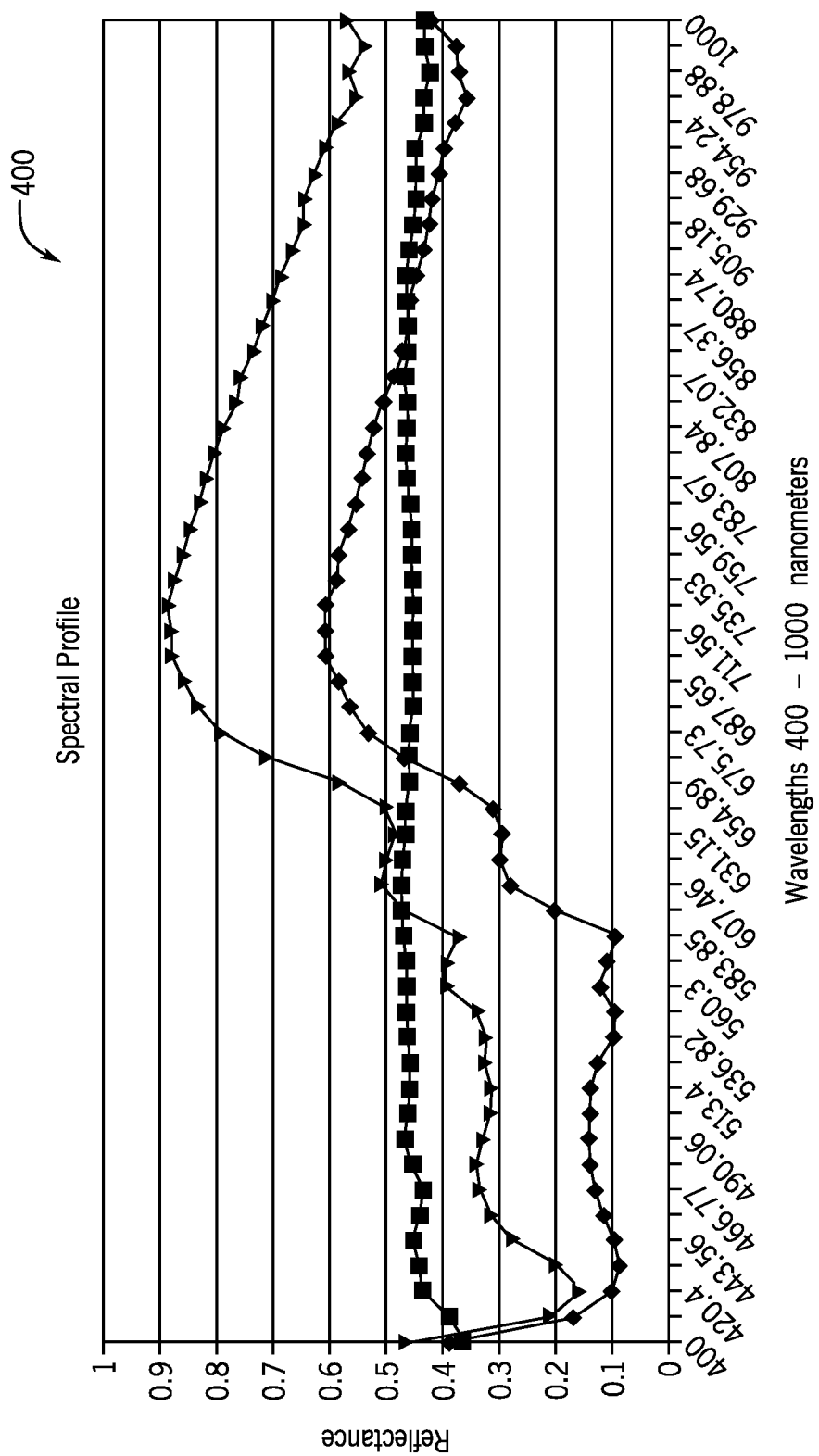
FIG. 4 illustrates a graph of that represents three different pixels each having a spectral profile according to an example embodiment.

FIG. 4 illustrates a graph 400 having three different lines that represent three different pixels having different spectral profiles. Each of the lines is associated with a different pixel of the hyperspectral image. As an example, each of the lines may indicate a pixel associated with an image of a banana. The lines may represent a brown pixel, a green pixel, and a yellow pixel, among other types of pixels. As is shown in FIG. 4, the graph shows a level of reflectance and an associated wavelength.

Figure 5:
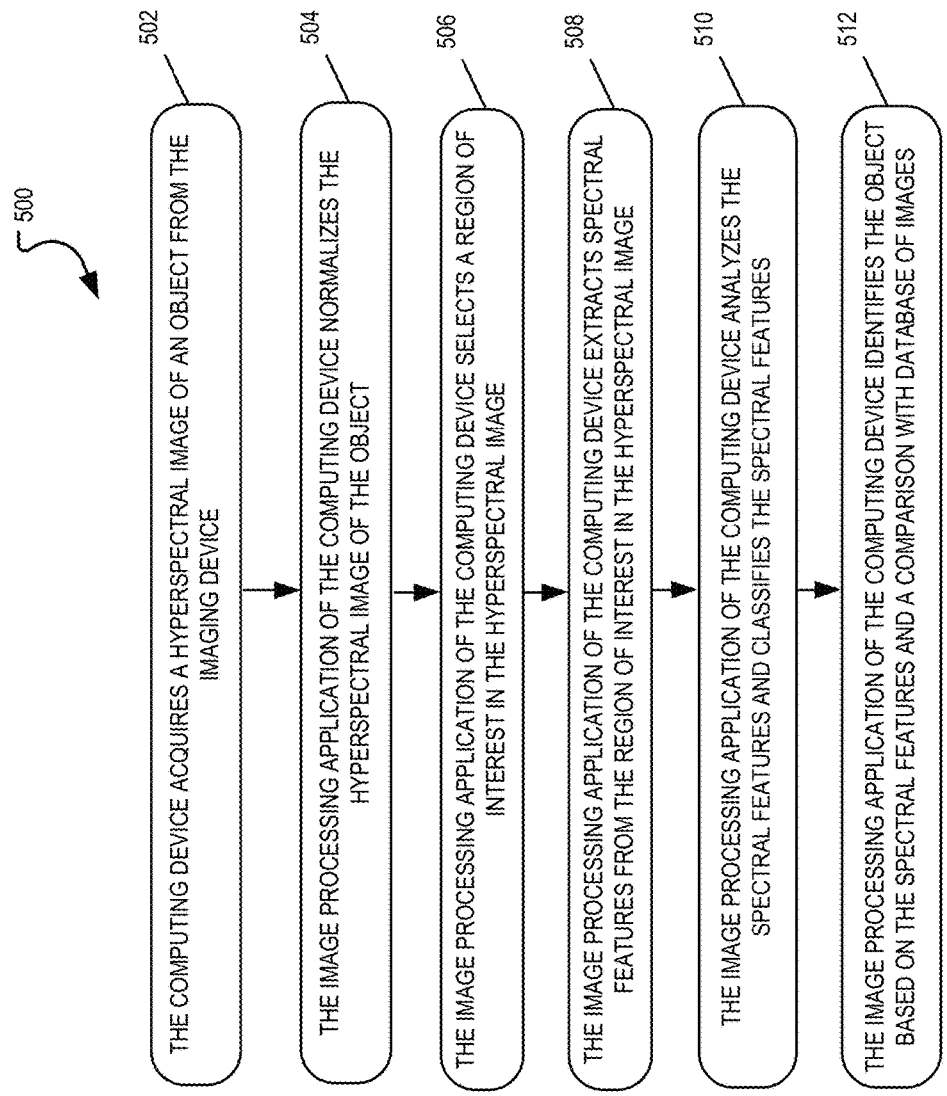
FIG. 5 illustrates a flowchart for performing hyperspectral image processing on an object according to an example embodiment.

FIG. 5 illustrates a flowchart of a process 500 for performing hyperspectral image processing on an object 104 according to an example embodiment. In step 502, the at least one computing device 110 acquires a hyperspectral image 105 of an object 104 from the imaging device 108. The hyperspectral image 105 of the object 104 may be a three-dimensional set of images of the object, each image in the set of images representing the object in a wavelength range of the electromagnetic spectrum. Next, in step 504, the image processing application 112 of the at least one computing device 110 normalizes the hyperspectral image of the object 104. In addition, the image processing application 112 of the at least one computing device 110 may compress the hyperspectral image 105 of the object 104.

In step 506, the image processing application 112 of the at least one computing device 110 selects a region of interest in the hyperspectral image 105. As an example, the region of interest may be selected in at least two of three dimensions of the image. In one example, the region of interest in the hyperspectral image 105 may include a representation of the object 104 in at least one wavelength range. In step 508, the image processing application 112 of the at least one computing device 110 may extract spectral features from the region of interest in the hyperspectral image of the object 104.

In step 510, the image processing application 112 of the at least one computing device 110 analyzes the spectral features of the region of interest and classifies the spectral features by comparing the hyperspectral image 105 with images and data in the synthetic dataset and using machine learning. This may include comparing the spectral features from the region of interest with the plurality of images in the training set to determine particular characteristics of the object. This may allow the image processing application 112 to classify and/or label the object in the image 105 (e.g., avocado) and in addition, this may include determining a value for at least one quality parameter for the object. As a result, the image processing application 112 may assign values to associated quality parameters of the object 104 such as dry matter, firmness, and ripeness, among others.

As an example, the image processing application 112 may determine the at least one quality parameter that may include dry matter content of the object 104, firmness of the object 104, and ripeness of the object 104 based on the classification of the spectral features. Each of the quality parameters may have at least one level of classification. Dry matter content may include a first level of classification when the dry matter content is under 21%, a second level of classification when the dry matter content is 21%, and a third level of classification when the dry matter content is above 21%. The image processing application 112 may assign a value between zero and one for each level of classification for each pixel in the region of interest.

Alternatively, this may include comparing the spectral features from the region of interest with the plurality of images in the training set to determine the presence of contaminants. This may be a contaminant such as plastic, paper, a metal hook, a cigarette butt, cardboard, textile, or another type of contaminant. Thus, this may include classifying spectral features found as foreign objects on the object.

In step 512, the image processing application 112 of the at least one computing device 110 may identify the object 104 and/or the foreign object 103 based on the classified spectral features and the comparison of the hyperspectral image 105 with the images and data in the synthetic dataset. This may be similar to comparing a hyperspectral fingerprint of the hyperspectral image 105 with the images and data in the synthetic dataset. This may include classifying and identifying the object as a food object. The food object or agricultural product may be one of an avocado, a banana, an orange, a peach, an onion, a pear, a kiwi fruit, a mango, berries, a tomato, an apple, sugar, pork, lamb, beef, or fish. In addition, this may include classifying and identifying plastic on frozen fish, classifying plastic on fruit such as an avocado, and classifying fibers or plastics in sugar.

Figure 6:
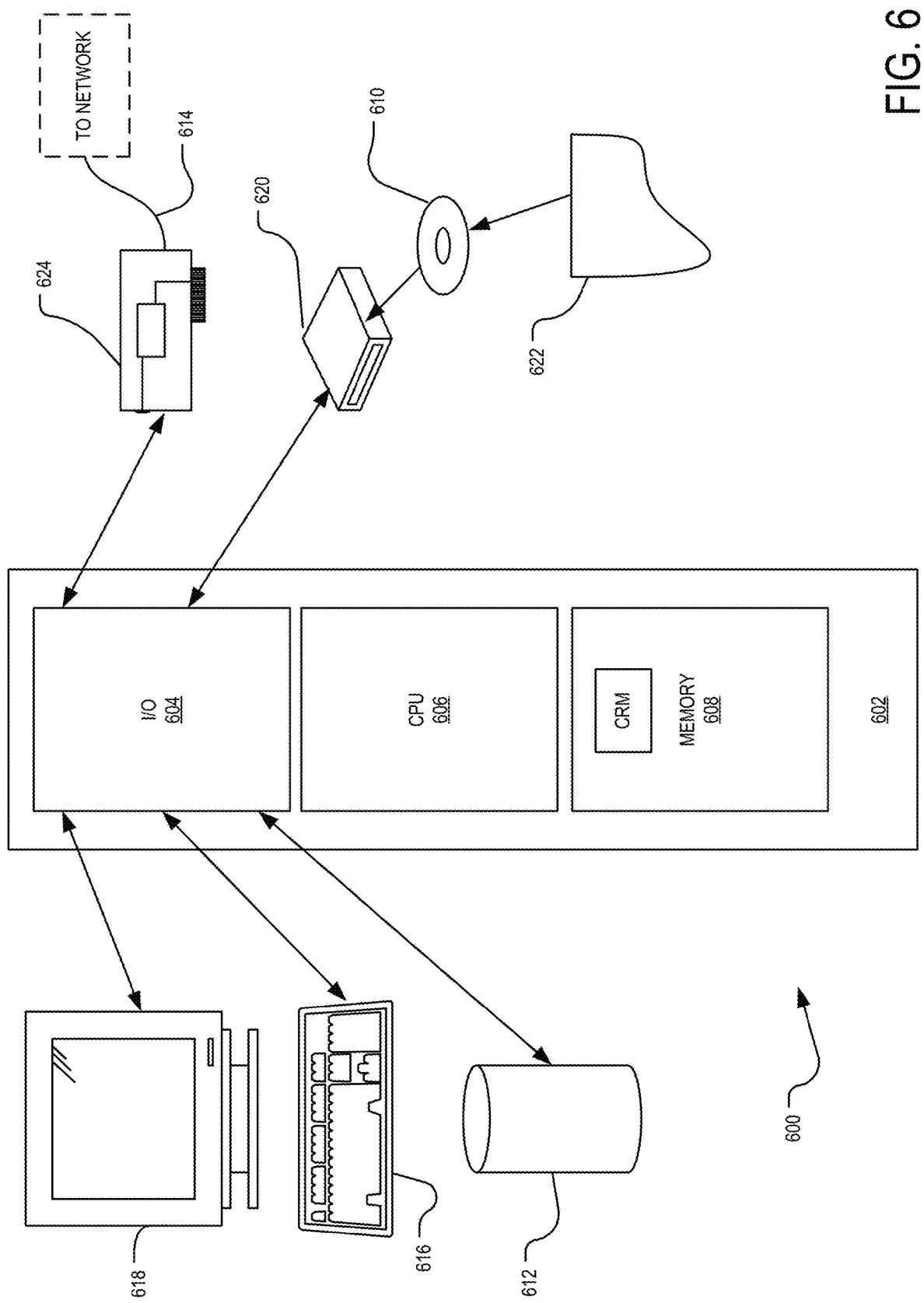
FIG. 6 illustrates a block diagram of a computing device according to an example embodiment.

FIG. 6 illustrates an example computing system 600 that may implement various systems, such as the computing device 110, and the methods discussed herein, such as process 300 and process 500. A general purpose computer system 600 is capable of executing a computer program product to execute a computer process. Data and program files may be input to the computer system 600, which reads the files and executes the programs therein such as the image processing application 112. Some of the elements of a general purpose computer system 600 are shown in FIG. 6 wherein a processor 602 is shown having an input/output (I/O) section 604, a central processing unit (CPU) 606, and a memory section 608. There may be one or more processors 602, such that the processor 602 of the computer system 600 comprises a single central-processing unit 606, or a plurality of processing units, commonly referred to as a parallel processing environment. The computer system 600 may be a conventional computer, a server, a distributed computer, or any other type of computer, such as one or more external computers made available via a cloud computing architecture. The presently described technology is optionally implemented in software devices loaded in memory 608, stored on a configured DVD/CD-ROM 610 or storage unit 612, and/or communicated via a wired or wireless network link 614, thereby transforming the computer system 600 in FIG. 6 to a special purpose machine for implementing the described operations.

The memory section 608 may be volatile media, nonvolatile media, removable media, non-removable media, and/or other media or mediums that can be accessed by a general purpose or special purpose computing device. For example, the memory section 608 may include non-transitory computer storage media and communication media. Non-transitory computer storage media further may include volatile, nonvolatile, removable, and/or non-removable media implemented in a method or technology for the storage (and retrieval) of information, such as computer/machine-readable/executable instructions, data and data structures, engines, program modules, and/or other data. Communication media may, for example, embody computer/machine-readable/executable, data structures, program modules, algorithms, and/or other data. The communication media may also include an information delivery technology. The communication media may include wired and/or wireless connections and technologies and be used to transmit and/or receive wired and/or wireless communications.

The I/O section 604 is connected to one or more user-interface devices (e.g., a keyboard 616 and a display unit 618), a disc storage unit 612, and a disc drive unit 620. Generally, the disc drive unit 620 is a DVD/CD-ROM drive unit capable of reading the DVD/CD-ROM medium 610, which typically contains programs and data 622. Computer program products containing mechanisms to effectuate the systems and methods in accordance with the presently described technology may reside in the memory section 604, on a disc storage unit 612, on the DVD/CD-ROM medium 610 of the computer system 600, or on external storage devices made available via a cloud computing architecture with such computer program products, including one or more database management products, web server products, application server products, and/or other additional software components. Alternatively, a disc drive unit 620 may be replaced or supplemented by a tape drive unit, or other storage medium drive unit. The network adapter 624 is capable of connecting the computer system 600 to a network via the network link 614, through which the computer system can receive instructions and data. Examples of such systems include personal computers, Intel or PowerPC-based computing systems, AMD-based computing systems, ARM-based computing systems, and other systems running a Windows-based, a UNIX-based, or other operating system. It should be understood that computing systems may also embody devices such as Personal Digital Assistants (PDAs), mobile phones, tablets or slates, multimedia consoles, gaming consoles, set top boxes, etc.

When used in a LAN-networking environment, the computer system 600 is connected (by wired connection and/or wirelessly) to a local network through the network interface or adapter 624, which is one type of communications device. When used in a WAN-networking environment, the computer system 600 typically includes a modem, a network adapter, or any other type of communications device for establishing communications over the wide area network. In a networked environment, program modules depicted relative to the computer system 600 or portions thereof, may be stored in a remote memory storage device. It is appreciated that the network connections shown are examples of communications devices for and other means of establishing a communications link between the computers may be used.

In an example implementation, source code executed by the computing device 110, a plurality of internal and external databases, source databases, and/or cached data on servers are stored in the memory of the computing device 110, or other storage systems, such as the disk storage unit 612 or the DVD/CD-ROM medium 610, and/or other external storage devices made available and accessible via a network architecture. The source code executed by the computing device 110 may be embodied by instructions stored on such storage systems and executed by the processor 602.

Some or all of the operations described herein may be performed by the processor 602, which is hardware. Further, local computing systems, remote data sources and/or services, and other associated logic represent firmware, hardware, and/or software configured to control operations of the hyperspectral image processing system 100 and/or other components. Such services may be implemented using a general purpose computer and specialized software (such as a server executing service software), a special purpose computing system and specialized software (such as a mobile device or network appliance executing service software), or other computing configurations. In addition, one or more functionalities disclosed herein may be generated by the processor 602 and a user may interact with a Graphical User Interface (GUI) using one or more user-interface devices (e.g., the keyboard 616, the display unit 618, and the user devices 604) with some of the data in use directly coming from online sources and data stores. The system set forth in FIG. 6 is but one possible example of a computer system that may employ or be configured in accordance with aspects of the present disclosure.

In the present disclosure, the methods disclosed may be implemented as sets of instructions or software readable by a device. Further, it is understood that the specific order or hierarchy of steps in the methods disclosed are instances of example approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure may be provided as a computer program product, or software, that may include a non-transitory machine-readable medium having stored thereon executable instructions, which may be used to program a computer system (or other electronic devices) to perform a process according to the present disclosure. A non-transitory machine-readable medium includes any mechanism for storing information in a form (e.g., software, processing application) readable by a machine (e.g., a computer). The non-transitory machine-readable medium may include, but is not limited to, magnetic storage medium (e.g., floppy diskette), optical storage medium (e.g., CD-ROM); magneto-optical storage medium, read only memory (ROM); random access memory (RAM); erasable programmable memory (e.g., EPROM and EEPROM); flash memory; or other types of medium suitable for storing electronic executable instructions.

The description above includes example systems, methods, techniques, instruction sequences, and/or computer program products that embody techniques of the present disclosure. However, it is understood that the described disclosure may be practiced without these specific details.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

While the present disclosure has been described with reference to various embodiments, it will be understood that these embodiments are illustrative and that the scope of the disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

What is claimed is:

1. A system comprising:
a memory; and
at least one processor to:
generate a synthetic training set comprising a plurality of hyperspectral images, the plurality of hyperspectral images based on actual hyperspectral images of an object, synthetic hyperspectral images of the object that include data added to the actual hyperspectral images of the object, and synthetic hyperspectral images of the object rendered in one of a different position and orientation;
acquire a hyperspectral image of the object by an imaging device, the hyperspectral image of the object comprising a three-dimensional set of images of the object, each image in the set of images representing the object in a wavelength range of the electromagnetic spectrum;
normalize the hyperspectral image of the object;
select a region of interest in the hyperspectral image, the region of interest comprising a subset of at least one image in the set of images;
extract spectral features from the region of interest in the hyperspectral image;
compare the spectral features from the region of interest with the plurality of hyperspectral images in the synthetic training set to determine particular characteristics of the object and determine a value for at least one quality parameter for the object; and
identify the object based on the spectral features.

2. The system of claim 1, the at least one processor further to train an object model using data comprising the plurality of hyperspectral images in the synthetic training set and ground truth measurements associated with the object and determine the particular characteristics of the object based on the object model.

3. The system of claim 1, the at least one processor further to determine dry matter content of the object, firmness of the object, and sugar content of the object.

4. The system of claim 1, wherein the imaging device comprises a hyperspectral imaging device and the system further comprises at least one illumination device that illuminates the object and a conveyor belt that moves the object past the imaging device as the hyperspectral imaging device captures the hyperspectral image.

5. The system of claim 1, wherein the object comprises a perishable food item.

6. The system of claim 5, wherein the perishable food item comprises an avocado.

7. The system of claim 1, wherein the object comprises an avocado and the at least one processor further to determine at least one of dry matter content of the avocado, firmness of the avocado, and sugar content of the avocado, based on the spectral features from the region of interest.

8. A method comprising:
generating, by a processor, a synthetic training set comprising a plurality of hyperspectral images, the plurality of images based on actual hyperspectral images of an object, synthetic hyperspectral images of the object that include data added to the actual hyperspectral images of the object, and synthetic hyperspectral images of the object rendered in one of a different position and orientation;
acquiring, by the processor, a hyperspectral image of the object by an imaging device, the hyperspectral image of the object comprising a three-dimensional set of images of the object, each image in the set of images representing the object in a wavelength range of the electromagnetic spectrum;
normalizing, by the processor, the hyperspectral image of the object;
selecting, by the processor, a region of interest in the hyperspectral image, the region of interest comprising a subset of at least one image in the set of images;
extracting, by the processor, spectral features from the region of interest in the hyperspectral image;
comparing, by the processor, the spectral features from the region of interest with the plurality of hyperspectral images in the synthetic training set to determine particular characteristics of the object and determining a value for at least one quality parameter for the object; and
identifying, by the processor, the object based on the spectral features.

9. The method of claim 8, further comprising training an object model using data comprising the plurality of hyperspectral images in the synthetic training set and ground truth measurements associated with the object and determining the particular characteristics of the object based on the object model.

10. The method of claim 8, further comprising determining dry matter content of the object, firmness of the object, and sugar content of the object.

11. The method of claim 8, the imaging device comprising a hyperspectral imaging device and the method further comprising illuminating the object by at least one illumination device and moving the object past the imaging device by a conveyor belt as the hyperspectral imaging device captures the hyperspectral image.

12. The method of claim 8, wherein the object comprises a perishable food item.

13. The method of claim 12, wherein the perishable food item comprises an avocado.

14. The method of claim 8, wherein the object comprises an avocado and the method further comprising determining at least one of dry matter content of the avocado, firmness of the avocado, and sugar content of the avocado, based on the spectral features from the region of interest.

15. A non-transitory computer-readable storage medium, having instructions stored thereon that, when executed by a computing device cause the computing device to perform operations, the operations comprising:

generating a synthetic training set comprising a plurality of hyperspectral images, the plurality of images based on actual hyperspectral images of an object, synthetic hyperspectral images of the object that include data added to the actual hyperspectral images of the object, and synthetic hyperspectral images of the object rendered in one of a different position and orientation;

acquiring a hyperspectral image of the object by an imaging device, the hyperspectral image of the object comprising a three-dimensional set of images of the object, each image in the set of images representing the object in a wavelength range of the electromagnetic spectrum;

normalizing the hyperspectral image of the object;

selecting a region of interest in the hyperspectral image, the region of interest comprising a subset of at least one image in the set of images;

extracting spectral features from the region of interest in the hyperspectral image;

comparing the spectral features from the region of interest with the plurality of hyperspectral images in the synthetic training set to determine particular characteristics of the object and determining a value for at least one quality parameter for the object; and identifying the object based on the spectral features.

16. The non-transitory computer-readable storage medium of claim 15, the operations further comprising training an object model using data comprising the plurality of hyperspectral images in the synthetic training set and ground truth measurements associated with the object and determining the particular characteristics of the object based on the object model.

17. The non-transitory computer-readable storage medium of claim 15, the operations further comprising determining dry matter content of the object, firmness of the object, and sugar content of the object.

18. The non-transitory computer-readable storage medium of claim 15, the imaging device comprising a hyperspectral imaging device and the operations further comprising illuminating the object by at least one illumination device and moving the object past the imaging device by a conveyor belt as the hyperspectral imaging device captures the hyperspectral image.

19. The non-transitory computer-readable storage medium of claim 15, wherein the object comprises a perishable food item.

20. The non-transitory computer-readable storage medium of claim 19, wherein the perishable food item comprises an avocado.

* * * * *